(12) United States Patent
Droske et al.

(10) Patent No.: US 9,187,596 B2
(45) Date of Patent: Nov. 17, 2015

(54) BIS-(HYDROXYALKYL)MERCAPTO-SUCCINATES

(76) Inventors: John P. Droske, Stevens Point, WI (US); Mark J. Juetten, Combined Locks, WI (US)

( * ) Notice: Subject to any disclaimer, the term of this patent is extended or adjusted under 35 U.S.C. 154(b) by 166 days.

(21) Appl. No.: 13/097,692

(22) Filed: Apr. 29, 2011

(65) Prior Publication Data

US 2011/0269903 A1    Nov. 3, 2011

Related U.S. Application Data

(60) Provisional application No. 61/329,325, filed on Apr. 29, 2010.

(51) Int. Cl.
| *C08G 63/688* | (2006.01) |
| *C07C 323/52* | (2006.01) |
| *C07C 323/54* | (2006.01) |
| *C07C 319/12* | (2006.01) |
| *C08L 67/00*  | (2006.01) |

(52) U.S. Cl.
CPC .......... *C08G 63/6886* (2013.01); *C07C 323/52* (2013.01)

(58) Field of Classification Search
CPC .................................................. C08G 63/688
USPC .............. 560/1, 147; 528/272, 274, 373, 374, 528/294, 377; 524/603
See application file for complete search history.

(56) References Cited

U.S. PATENT DOCUMENTS

2009/0297607 A1    12/2009    Wang et al.

OTHER PUBLICATIONS

Kato et al., "Direct Enzymatic Synthesis of a Polyester with Free Pendant Mercapto Groups," Biomacromolecules 2009, 10, 366-373.
Seabra et al., "Polynitrosated Polyesters: Preparation, Characterization, and Potential Use for Topical Nitric Oxide Release," Biomacromolecules 2005, 6, 2512-2520.
Yamamoto et al., "Preparation of Gelatinous Reversible Addition—Fragmentation Chain Transfer Agents "RAFT Gel" via Chemoselective Polycondensations of a Dicarboxylic Acid Containing a Mercapto Group and Diols," Macromolecules 2010, 43, 8519-8523.

*Primary Examiner* — Duc Truong
(74) *Attorney, Agent, or Firm* — Don D. Cha; Hamilton DeSanctis & Cha, LLP

(57) ABSTRACT

The present invention provides bis(hydroxyalkyl)mercaptosuccinates of the formula:

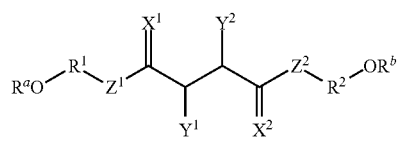

and derivatives thereof, where $X^1$, $X^2$, $Z^1$, $Z^2$, $Y^1$, $Y^2$, $R^a$, $R^b$, $R^1$, and $R^2$ are those defined herein. The present invention also provides methods for producing and using the same.

17 Claims, No Drawings

BIS-(HYDROXYALKYL)MERCAPTO-SUCCINATES

CROSS-REFERENCE TO RELATED APPLICATIONS

This application claims the priority benefit of U.S. Provisional Application No. 61/329,325, filed Apr. 29, 2010, which is incorporated herein by reference in its entirety.

FIELD OF THE INVENTION

The present invention relates to bis(hydroxyalkyl)mercaptosuccinates and derivatives thereof, and methods for producing and using the same.

BACKGROUND OF THE INVENTION

Mercapto functional groups are useful in polymer crosslinking. They can be readily crosslinked using an oxidizing agent or via a free radical reaction to form a disulfide linkage. The disulfide linkage can be reversibly cleaved, for example, by using a reducing agent. Such a reversible crosslinking property has been used to synthesize a wide variety of bioresorbable polymers including hydrogels.

In this regard, mercapto succinic acid and its derivative should offer an attractive way to prepare a wide variety of polymers with sulfur pendant groups for further crosslinking, for example, in bioresorbable and hydrogel materials. They also may find use in applications such as "permanent" type hair treatments or as metal scavengers (say in resolving cadmium or other heavy metal poisoning or in removing cadmium or other heavy metal pollutants from a waste stream or other source).

Accordingly, there is a need for mercapto succinic acids and derivatives that are useful in polymerization.

SUMMARY OF THE INVENTION

Some aspects of the invention provide a compound of the formula:

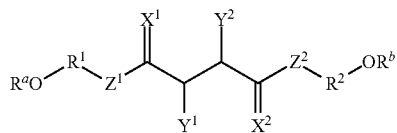

where
each of $X^1$, $X^2$, $Z^1$, and $Z^2$ is independently $NR^3$, O, $P(O)_a(OR^z)_b$, Se, or S;
$Y^1$ is —$S(O)_n R^4$;
$Y^2$ is H, $C_1$-$C_6$ alkyl, or —$S(O)_n R^4$;
a is 0 or 1 such that when a is 0, b is an integer from 1 to 3 and when a is 1, b is 0 or 1;
n is an integer from 0 to 4;
each $R^z$ is independently H, or alkyl;
each of $R^a$ and $R^b$ is independently H, alkyl, aryl, heteroaryl, or a hydroxy protecting group;
each of $R^1$ and $R^2$ is independently alkylene, heteroalkylene, haloalkylene, cycloalkylene, arylene, or heteroarylene;
each of $R^3$ is independently H, alkyl, aryl, heteroaryl, or a nitrogen protecting group; and
each of $R^4$ is independently H, alkyl, aryl, or heteroaryl.

Other aspects of the invention provide methods for producing the same and polymers, including copolymers, derived from the same.

DETAILED DESCRIPTION OF THE INVENTION

"Alkyl" refers to a saturated linear monovalent hydrocarbon moiety of one to twenty, typically one to twelve, carbon atoms or a saturated branched monovalent hydrocarbon moiety of three to twenty, typically three to twelve, carbon atoms. Exemplary alkyl group include, but are not limited to, methyl, ethyl, n-propyl, 2-propyl, tert-butyl, pentyl, and the like.

"Aryl" refers to a monovalent mono-, bi- or tricyclic aromatic hydrocarbon moiety of 6 to 15 ring atoms which is optionally substituted with one or more, typically one, two, or three substituents within the ring structure. When two or more substituents are present in an aryl group, each substituent is independently selected.

"Cycloalkyl" refers to a non-aromatic, generally saturated, monovalent mono- or bicyclic hydrocarbon moiety of three to twenty ring carbons. The cycloalkyl can be optionally substituted with one or more, typically one, two, or three, substituents within the ring structure. When two or more substituents are present in a cycloalkyl group, each substituent is independently selected.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —$CH_2Cl$, —$CF_3$, —$CH_2CF_3$, —$CH_2CCl_3$, and the like.

The term "heteroalkyl" means a branched or unbranched, acyclic saturated alkyl moiety containing carbon, hydrogen and one or more heteroatoms, such as O, N, or S, in place of a carbon atom. Representative examples include, but are not limited to, ethers, thioethers, amino substituted alkyls, etc.

The term "heteroaryl" means a monovalent monocyclic or bicyclic aromatic moiety of 5 to 12 ring atoms containing one, two, or three ring heteroatoms selected from N, O, or S, the remaining ring atoms being C. The heteroaryl ring is optionally substituted independently with one or more substituents, typically one or two substituents. Exemplary heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

The terms "alkylene", "arylene", "cycloalkylene", "haloalkylene", "heteroalkylene", and "heteroarylene" refer to a divalent alkyl, aryl, cycloalkyl, haloalkyl, heteroalkyl, and heteroaryl, respectively, as defined herein.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3rd edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom to which it is attached.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Compounds of the Invention

Some aspects of the invention provide a compound of the formula:

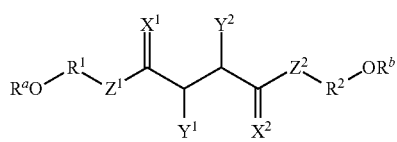

I where
each of $X^1$, $X^2$, $Z^1$, and $Z^2$ is independently $NR^3$, O, $P(O)_a(OR^z)_b$, Se, or S;
$Y^1$ is $—S(O)_nR^4$;
$Y^2$ is H, $C_1$-$C_6$ alkyl, or $—S(O)_nR^4$;
a is 0 or 1 such that when a is 0, b is an integer from 1 to 3 and when a is 1, b is 0 or 1;
n is an integer from 0 to 4;
each $R^z$ is independently H or alkyl;
each of $R^a$ and $R^b$ is independently H, alkyl, aryl, heteroaryl, or a hydroxy protecting group;
each of $R^1$ and $R^2$ is independently alkylene, heteroalkylene, haloalkylene, cycloalkylene, arylene, or heteroarylene;
each of $R^3$ is independently H, alkyl, aryl, heteroaryl, or a nitrogen protecting group; and
each of $R^4$ is independently H, alkyl, aryl, or heteroaryl.

In some embodiments, each of $X^1$, $X^2$, $Z^1$, and $Z^2$ is independently $NR^3$, O, or S. Within these embodiments, in some instances $X^1$ and $X^2$ are O.

Still in other embodiments, $Y^2$ is H or $—S(O)_nR^4$. Within these embodiments, in some instances, $Y^2$ is $—S(O)_nR^4$. In some cases, n is 0. Still in other cases, $R^4$ is H.

Yet in other embodiments, $Y^2$ is H.

In other embodiments, $Y^1$ is $—S(O)_nR^4$. Within these embodiments, often n is 0. Still in other cases $R^4$ is H.

Still yet in other embodiments, $Z^1$ and $Z^2$ are O.

In other embodiments, each of $R^1$ and $R^2$ is independently $C_2$-$C_{20}$ alkylene. Within these embodiments, in some cases each of $R^1$ and $R^2$ is independently ethylene, propylene, butylene, pentylene, hexylene, heptylene, octylene, nonylene, 10-hydroxydecyl, or an isomer or derivative thereof.

Still in other embodiments, $R^a$ and $R^b$ are H.

Still further, combinations of various specific groups described herein form other embodiments. For example, in one particular embodiment $X^1$, $X^2$, $Z^1$ and $Z^2$ are O, and $Y^2$ is $—S(O)_nR^4$, n is 0, and $R^4$ is H. In this manner, a variety of compounds are embodied within the present invention.

Synthesis

The compounds of the present invention can be prepared by a variety of methods. It should be appreciated that although the following schemes for producing compounds of Formula I often indicate exact structures, methods of the present invention apply widely to analogous compounds of Formula I, given an appropriate consideration to protection and deprotection of reactive functional groups by methods standard to the art of organic chemistry. For example, hydroxy groups, in order to prevent unwanted side reactions, sometimes need to be converted to ethers or esters during chemical reactions at other sites in the molecule. The hydroxy protecting group is then removed to provide the free hydroxy group. Similarly, amino groups and carboxylic acid groups can be derivatized to protect them against unwanted side reactions. Typical protecting groups, and methods for attaching and cleaving them, are described fully in the above incorporated references by T. W. Greene and P. G. M. Wuts, *Protective Groups in Organic Synthesis*, 3rd edition, John Wiley & Sons, New York, 1999, and Harrison and Harrison et al., *Compendium of Synthetic Organic Methods*, Vols. 1-8 (John Wiley and Sons, 1971-1996).

In some aspects of the invention, a method for preparing compounds of Formula I is shown in Scheme 1 below:

Scheme 1

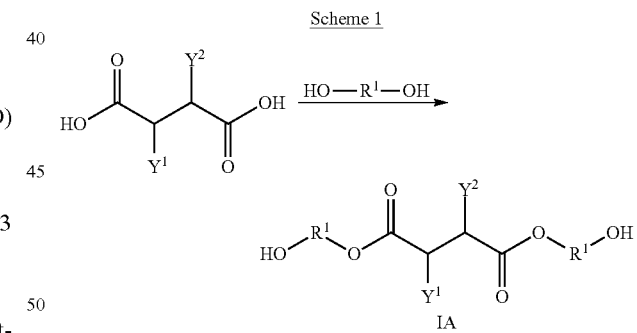

where
$Y^1$ is $—S(O)_nR^4$;
$Y^2$ is H, $C_1$-$C_6$ alkyl, or $—S(O)_nR^4$;
n is an integer from 0 to 4;
$R^1$ is an alkylene, heteroalkylene, haloalkylene, cycloalkylene, arylene, or heteroarylene;
each of $R^4$ is independently H, alkyl, aryl, or heteroaryl.

In some embodiments, n is 0 and $R^4$ is H. In other embodiments, $Y^2$ is H or $—S(O)_nR^4$. Still in other embodiments, $Y^2$ is H or —SH.

Typically, at least 2 molar equivalents of the diol is used relative to the succinic acid compound. In this manner, stoichiometrically the desired product is favored. If only 1 equivalent of the diol is used, it is possible that a diol will react with two succinic acid molecules, thereby leading to other products. Generally, an excess amount of diol is used to favor the formation of compounds of Formula IA, although a high molecular weight polymer containing thiol pendant groups can be prepared by using stoichiometric amounts of succinic acid (or succinyl chloride) with the diol under the conditions described herein.

Surprisingly and unexpectedly, the inventors have found that the coupling reaction can be achieved with a wide variety of esterification reaction conditions known to one skilled in the art. It is generally known to one skilled in the art that a thiol group is typically more reactive (e.g., more nucleophilic) than a hydroxy group. Therefore, one skilled in the art would expect such an esterification of mercapto succinic acid with an alcohol would lead to a thiolester formation rather than an ester formation.

In some embodiments, the succinic acid is reacted with the diol in the presence of an acid catalyst to produce compound of Formula IA. In some instances, the acid catalyst comprises a metal halide. Suitable acid catalysts include, but are not limited to, zinc chloride, sulfuric acid, stannous octoate or a derivative thereof, tin chloride, or a mixture thereof. The reaction temperature can range widely and can be readily optimized by one skilled in the art. When metal halide is used, the initial reaction temperature is typically about 0° C. or lower, typically −20° C. or lower, and often around −78° C. Generally, the reaction temperature is then slowly allowed to reach room temperature over a period of time. Typical solvents include inert organic solvents such as methylene chloride, chloroform, ether, or toluene. The amount of acid catalyst used can vary widely, but in some cases one molar equivalent or more can be used, if the catalyst is converted to another species during the reaction. This is particularly applicable when a metal halide is used to catalyze the esterification reaction.

In other embodiments, the succinic acid is reacted with the diol in the presence of a coupling reagent. Many coupling agents are known to one skilled in the art. In some instances, the coupling reagent comprises a carbodiimide. Typically, a non-nucleophilic base such as triethylamine, diisopropylethylamine, or the like is added to the reaction mixture to neutralize any acidic proton that is formed during the reaction. Suitable carbodiimides include, but are not limited to, dicyclocarbodiimide, diisopropylcarbodiimide, 1-ethyl-3-(3-dimethylaminopropyl)carbodiimide, or a mixture thereof. Typically, the initial reaction temperature is about 0° C. or lower, often about −20° C. or lower, and more often about −78° C. The reaction temperature is then typically allowed to reach room temperature over a period of time. Typical solvents for this reaction include, but are not limited to, methylene chloride, chloroform, ether, tetrahydrofuran (THF), or toluene. The amount of carbodiimide used is generally at least two equivalents relative to the amount of succinic acid. The amount of non-nucleophilic base used is often such that there is an excess amount to ensure substantially complete scavenging of any acid that is produced during the reaction.

The yield of compound of Formula IA is at least 20%, typically at least 40%, often at least 60%, and more often at least about 75%.

Utility

Compounds of the invention are useful in a wide variety of applications including as a monomer or a comonomer in production of various polymers or copolymers, respectively. Accordingly, some aspects of the invention include polymers derived from compounds of the invention. Typically, polymers produced using compounds of the invention are biocompatible polymers, hydrogels, and other biologically useful polymers. Moreover, because compounds of the invention comprise one or more thiol groups, the resulting polymers can be cross-linked to form a disulfide linkage. There are many methods for cross-linking thiols to form a disulfide linkage, e.g., photolysis, oxidation, etc. A wide variety of suitable oxidizing agents are known to one skilled in the art to form a disulfide from thiol functional groups. Exemplary oxidizing agents for forming a disulfide linkage include, but are not limited to, hydrogen peroxide (alone or in the presence of ferrous citrate, copper (II), or other metal complexes), iodine in the presence of base, dimethyl sulfoxide in the presence of air, oxygen alone or in the presence of suitable catalysts, and thiol-disulfide exchange reactions.

As stated above, compounds of the invention can also be used as a comonomer in production of various copolymers and dendrimers. Accordingly, exemplary copolymers and dendrimers of the invention include, but are not limited to, copolymers of polyethylene glycol (PEG), polycarbonates such as by reaction with phosgene, polyethers, polyepoxides, and polyether-ether-ketones, polyurethanes such as by reaction with bisisocyanates such as toluene diisocyanate, polyesters by reaction with phthalates, isophthalates, terephthalates, oxalates, malonates, sebacates, succinates, fumarates, lactates, and glycolates, polyacrylates and methacrylates, polysulfides and polydisulfides, polyisobutylene, polybutylene, polyvinylchloride (PVC), polyethylene, polystyrene, and polypropylene, and the like.

As stated above, polymers derived from compounds of the invention can be cross-linked to form a disulfide linkage. The formation of disulfide linkage is often reversible, and therefore allows one to selectively cleave the disulfide linkages. For example, disulfides can be cleaved to regenerate thiol groups by reacting with a reducing agent. Exemplary reducing agents that are suitable for cleaving disulfide linkage include, but are not limited to, dithiothreitol (DTT), thioglycerol, glutathione, 2-mercaptoethanol, 2-mercaptoethylamine, cysteine, thioglycolic acid, and alkyl and carboxyalkylphosphines.

In some embodiments, the polymerization reaction to form the oligomers and polymers containing thiol pendant groups did not require solvent. In addition, such polymerization reaction was achieved using a reusable catalyst.

In other aspects of the invention, crosslinking the thiol groups of the oligomers provides a wide variety of polymeric materials such as polymer films, as well as other crosslinked polyesters. Surprisingly and unexpectedly, physical properties of crosslinked polymers of the invention include, depending on a variety of factors such as the amount of crosslinking, the diol used, the molecular weight of the polymer, crosslinking catalyst used, etc., clear and colorless films, optically translucent films, soft and flexible polymers, hard and brittle polymers, hard and tough polymers as well as various combinations thereof. As used herein, "clear and colorless" refers to having a visible light transmission similar to (e.g., at least 80%, typically at least 90%, often at least 95%, and more often substantially identical to) that of glass. The term "optically translucent" refers to a polymer that allows light to pass through but not detailed images.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

General Crosslinking Procedure

A neat sample with a mass of 1 to 5 g was poured onto a clean, flat and level, 8×8 inch glass pane. For viscous samples, the sample was first warmed to facilitate pouring or was dissolved in methylene chloride to make an ~10% solution. The sample was allowed to spread across the plate by gravity or using a doctor's knife (i.e., a metal blade or glass rod with spacers on both ends). The plate was placed into an oven in air at (e.g., 100-160° C., typically 100-110° C.) until the sample cured into a film (typically one to several days). If solvent was used, the lightly covered plate was allowed to stand overnight in a hood to remove solvent before being placed in the oven. After cooling, the resultant films were removed from the plate.

Example 1

This example illustrates one method for synthesizing bis (5-hydroxypentyl)-2-mercaptosuccinate.

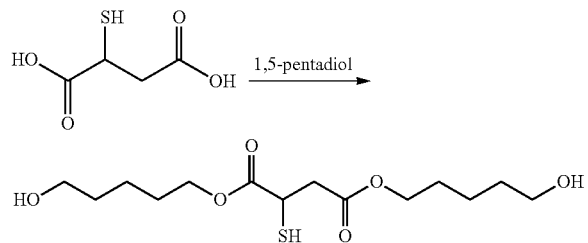

To a round bottom flask equipped with a condenser and with magnetic stirring, was added 1.61 grams (0.0108 mole) of mercaptosuccinic acid, 40.0 mL (0.382 mole) of 1,5-pentanediol, and 0.015 g (0.000108 mole) of zinc chloride. The apparatus was flushed with nitrogen for 5-10 minutes and then maintained under a static nitrogen atmosphere. The reaction mixture was heated at 150° C./hour to 155° C. and then maintained at 155° C. for 4 hours. After cooling to room temperature, 100 mL of methylene chloride was added to dissolve the product. The solution was washed 2× with 100 mL of distilled water and 2× with 100 mL of 50% saturated NaCl. The organic layer was dried over sodium sulfate and the solvent was removed via rotary evaporation. Residual solvent was removed under vacuum (less than 1 mm Hg) at or slightly above ambient temperature and the structure was confirmed by IR, $^1$HNMR, and $^{13}$CNMR spectroscopy.

Example 2

This example illustrates one method for synthesizing oligo-bis(5-hydroxypentyl)-2-mercaptosuccinate and producing a polymeric film using the same.

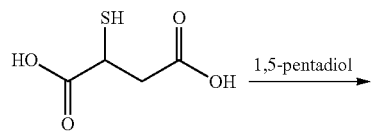

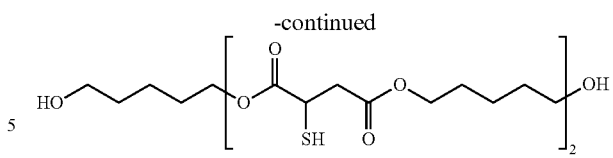

The procedure was similar to Example 1 above procedure for the preparation of bis(5-hydroxypentyl)-2-mercaptosuccinate, except 7.54 grams (0.0502 mole) of mercaptosuccinic acid, 15.7 mL (0.150 mole) of 1,5-pentanediol, and 0.1742 grams (0.00128 mole) of zinc chloride were used. The structure of the product again was confirmed by IR, $^1$HNMR, and $^{13}$CNMR spectroscopy.

Heating the resulting product for 4 hours at 155° C. under vacuum afforded a polymer. One particular experimental procedure for producing the polymer film is as follows: To a round bottom flask equipped for distillation and magnetic stirring, was added 3.7028 grams of oligomer produced in Example 2 and 0.1486 g (10.90 mmole) of zinc chloride. The apparatus was flushed with nitrogen for 5-10 minutes and then maintained under a flowing nitrogen atmosphere. The reaction mixture was heated at 150° C. for one hour and the temperature was increased to 155° C. and then maintained at 155° C. for 4 hours. After cooling to room temperature, 80 mL of methylene chloride was added to dissolve the product. The solution was washed 2× with 50 mL of distilled water and 2× with 50 mL of saturated aqueous NaCl solution. The organic layer was dried over anhydrous sodium sulfate and the solvent was removed via rotary evaporation. Residual solvent was removed under vacuum (less than 1 mm Hg) at or slightly above ambient temperature and the structure was confirmed by IR, $^1$HNMR, and $^{13}$CNMR spectroscopy.

This viscous polymer was poured onto a glass plate and allowed to crosslink in air for four days at 110° C. to afford a clear, colorless, flexible polymer film.

As shown herein, the oligomeric diols comprising pendant thiol groups can be polymerized to higher molecular weight products simply by heating in the presence of catalyst. This makes methods of the present invention compatible with existing industrial processes for the preparation of polyesters, e.g., commercial polyethylene terephthalate (PET, recycling code #1). Accordingly, methods of the invention can be used to synthesize oligomers from diol-terminated compounds disclosed herein that, upon heating in the presence of a catalyst, extrude or produce aliphatic diols (like ethylene glycol) to form high molecular weight polymers.

Example 3

The above procedures is modified to afford a series of diols containing pendant thiol groups by changing the diol that is used. For example, in addition to the thiol-containing pentylene diols reported above, the analogous butylene diols were also synthesized. In addition, analogous compounds from other diols are prepared.

Example 4

The above procedures are readily modified for the preparation of the analogous dithio-substituted diols by substituting 2,3-dimercaptosuccinic acid for mercaptosuccinic acid.

Example 5

The diols were chain extended by allowing them to react with succinyl chloride with methylene chloride as solvent. This afforded polyesters containing pendant thiol groups.

Example 6

This example illustrates one procedure for the preparation of covalently-bonded, crosslinked polymers that readily reverse to linear polymers.

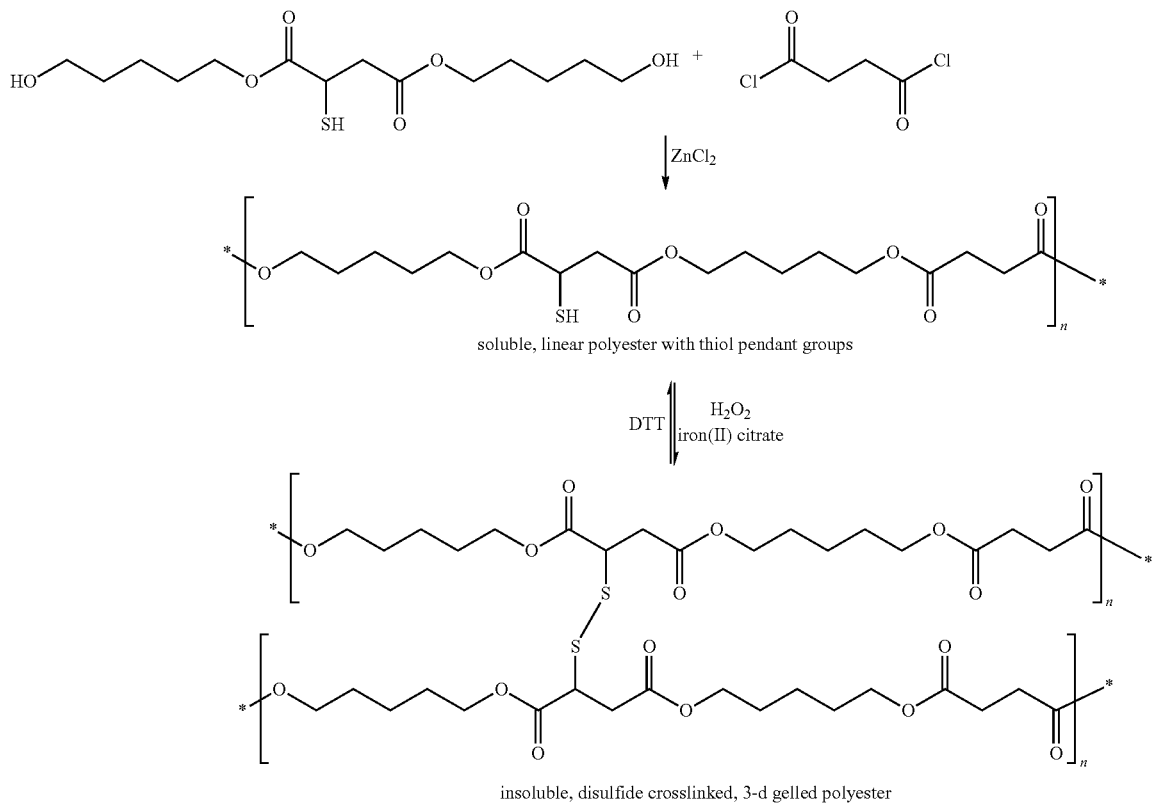

soluble, linear polyester with thiol pendant groups insoluble, disulfide crosslinked, 3-d gelled polyester Chain Extension Reaction and Film Formation To a round bottom flask equipped with a magnetic stir bar and argon inlet and outlet, was added 4.5 grams (0.0089 mole) of oligo-bis(5-hydroxypentyl)-2-mercaptosuccinate (or 0.0089 mole of oligo-bis(5-hydroxypentyl)-2-mercaptosuccinate) and 10 mL of dry methylene chloride. The reaction mixture was cooled in an ice bath for 30 minutes, and then 1.38 grams, about 1 mL, (0.0089 mole) of succinyl chloride was added via syringe or cannula (dropwise or in one portion). After the addition of succinyl chloride, stirring was continued in for 12 hours with a slow argon purge into a distilled water bubbler to remove HCl. About halfway through the stirring, the water in the bubbler was changed. Methylene chloride was removed using a rotary evaporator and the viscous product was precipitated in ice-cold diethyl ether or methanol under vigorous stirring. The product was collected by vacuum filtration, air-dried for 24 hours and then residual solvent was removed under reduced pressure (less than 1 mm Hg) at or slightly above ambient temperature. The chain extended product was characterized by FTIR, $^1$HNMR, $^{13}$CNMR spectroscopy, and gel permeation chromatography with triple detection (laser light scattering, viscometry, and refractive index). Clear, colorless films could be cast from chloroform. After drying, the films were of a high quality and did not fail when subjected to a fingernail crease test.

The crosslinking afforded high quality films. For example, the present inventors have found that heating the polyesters described above containing pendant thiols on glass plates in air at temperatures of approximately 100-110° C. for several days gave excellent quality films with a wide range of properties, depending on the composition of the polyester. This is a significant improvement to the conventional chain extension and film formation approach.

The present inventors have found that depending on the composition, the resultant films range from having clear colorless optical properties, or outstanding optical clarity similar to Plexiglas® (polymethyl methacrylate) or Lexan® (polycarbonate) plastics, or being translucent. Due to different compositions, the properties of polymeric films of the present invention can range from hard, brittle materials to hard, tough materials (e.g., like those used to make a plastic milk jug or a guitar pick) to soft, flexible elastomers. In some instances, the elastomers exhibit properties similar to those of a typical rubber band, yet they are colorless and very transparent. These physical and optical properties are surprising and unexpected and allow polymers of the present invention to be used in a wide variety of applications including, but not limited to, as soft contact lenses. The soft, flexible materials also can be used as tissue scaffolds or as tissue replacements, such as skin grafting applications. The adhesion properties of some of the polymers of the invention are excellent and as such these polymers can also be used as high quality, degradable adhesives.

In some instances, when partially crosslinked, polymers of the present invention can also be used as anti-oxidant film barriers, since residual thiol groups can react with gaseous oxygen to prevent its passage through the film. Similarly, polymers of the present invention (e.g., polymer films) can also be used as "oxygen scrubbers" for removing trace amounts of oxygen from nitrogen, argon, or other gases.

Redox Reactions (for Crosslinking and Reversing of Crosslinking)

Crosslinking of the pendant thiol groups of the product above was effected in methylene chloride using hydrogen peroxide and ferrous (II) citrate. The pH was adjusted to about pH 9 using sodium bicarbonate. The oxidation reaction continued for 30 minutes at room temperature resulting in a methylene chloride-insoluble solid product. After isolation, the insoluble product, in methylene chloride, was treated with dithiothreitol (DTT), resulting in a clear solution of dissolved polymer. In addition to the solid polymer described here, film samples of the above also were subjected to this crosslinking reaction. This resulted in a transition from the clear, colorless film described above to a white, methylene chloride-insoluble film.

Example 7

This example illustrate an oxidation, chain extension, and reduction reactions to reversibly form a polymer network from an "H-shaped" tetrafunctional alcohol from bis(5-hydroxypentyl)-2-mercaptosuccinate.

the bis(5-hydroxypentyl)-2-mercaptosuccinate mixture while stirring. The oxidation reaction continued for 30 minutes at room temperature. After completion of reaction, the aqueous layer was removed and the organic layer was dried over anhydrous sodium sulfate. Organic solvent was removed from the product via rotary evaporation and residual solvent was removed under reduced pressure (less than 1 mm Hg) at, or slightly above, ambient temperature. Completion of the oxidation reaction was monitored by FTIR.

Chain Extension Polyesterification Reaction

To a round bottom flask equipped with a magnetic stir bar and fitted with a drying tube charged with anhydrous calcium carbonate, was added 3 grams of the "H-shaped" tetrafunctional oxidized bis(5-hydroxypentyl)-2-mercaptosuccinate (or oligo-bis(5-hydroxypentyl)-2-mercaptosuccinate) and 6 mL of dry methylene chloride. The reaction mixture was cooled by an ice bath for 30 minutes, and upon cooling, 1.38 grams, about 1 mL, of succinyl chloride was added via syringe dropwise over 20 minutes. Upon completion of the addition of succinyl chloride, the reaction mixture was stirred in ice bath until the gel point was reached (~30 minutes). After

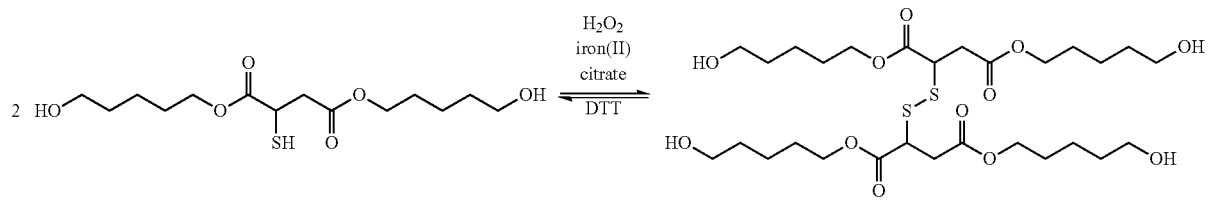 [SMILES: O=C(CC(S)C(=O)OCCCCCO)OCCCCCO ; "DTT" ; O=C(CC(SSC(CC(=O)OCCCCCO)C(=O)OCCCCCO)C(=O)OCCCCCO)OCCCCCO]

Oxidation Reaction to Form an "H-Shaped" Disulfide Containing Four Hydroxy Functional Groups To a 20 mL glass vial was added 6 grams of hydrogen peroxide and 0.051 grams of ferrous (II) citrate. This oxidation solution was mixed and brought to about pH 9 using sodium bicarbonate. To a 20 mL glass vial equipped with a magnetic stir bar was added 3.7 grams of bis(5-hydroxypentyl)-2-mercaptosuccinate and 5 mL of methylene chloride. The oxidation solution was added dropwise over 5 minutes to gelation, 50 mL of methylene chloride was added to the gelled polymer. The polymer was then broken up and the gelled polymer and solvent were transferred to a separatory funnel for further purification. The gelled polymer/methylene chloride mixture was washed 2× with 50 mL of distilled water, 10 mL of 5% HCl, and again with 50 mL of distilled water. The aqueous layer was removed and the organic layer was dried over anhydrous sodium sulfate.

Reduction Reaction (Reversing of Crosslinking)

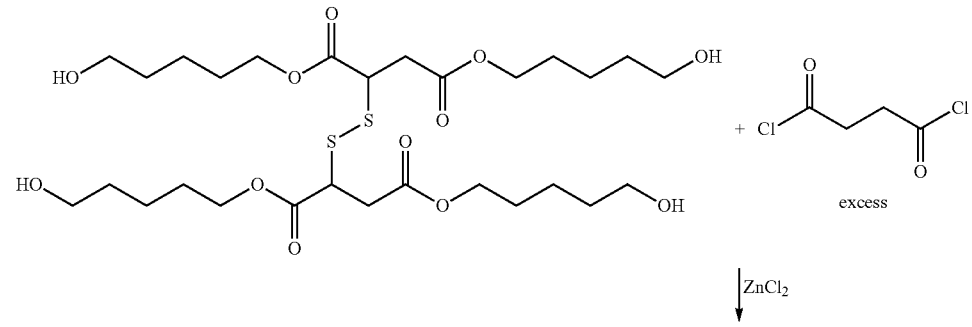

-continued

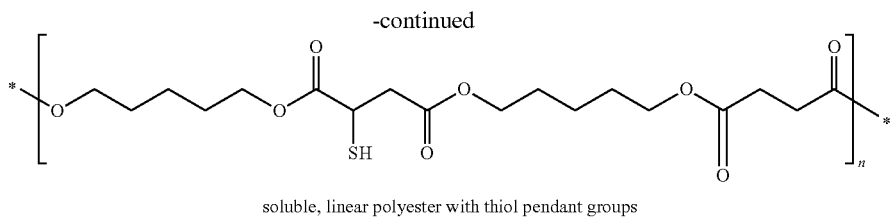

soluble, linear polyester with thiol pendant groups

After the washings described above, the heterogeneous mixture of methylene chloride and the methylene chloride-insoluble gelled polymer was treated with dithiothreitol (DTT). The mixture was shaken and additional DTT was added in portions until all of the gelled polymer was in solution. The methylene chloride was removed using a rotary evaporator under reduced pressure resulting in a yellow powder. The powder was dissolved in methylene chloride and characterized by gel permeation chromatography with triple detection (laser light scattering, viscometer, and refractive index).

Example 8

Linear polyesters were synthesized by reacting 3-mercaptosuccinic acid with various alkylene diols under stoichiometrically equivalent conditions. All of the monomers used are commercially available. The reactions were carried out without the need for protection and deprotection of the thiol functional group. The stoichiometric equivalent reaction was used to produce a series of polymers that formed films. These polymers can be reversibly crosslinked in a similar manner as the chain extended polymers described above.

For example 90% 3-mercaptosuccinic acid (MSA) and 10% succinic acid (SA) copolymer as well as linear polyester copolymers with other MSA:SA ratios such as 75:25; 50:50; 33:66; 25:75; and 10:90 were prepared as described below by adjusting the amount of MSA and SA. In addition, various diols, such as 1,2-ethylene glycol, 1,4-butanediol, and 1,6-hexanediol, also have been used in place of 1,5-pentanediol.

To a round bottom flask equipped for distillation and magnetic stirring, was added 13.51 grams (90.00 mmole) of mercaptosuccinic acid, 1.181 grams (10.00 mmole) of succinic acid, 10.41 g (100.0 mmole) of 1,5-pentanediol, and 0.1363 g (10.00 mmole) of zinc chloride. The apparatus was flushed with nitrogen for 5-10 minutes and then maintained under a flowing nitrogen atmosphere. The reaction mixture was heated at 150° C./hour to 155° C. and then maintained at 155° C. for 4 hours. After cooling to room temperature, 200 mL of methylene chloride was added to dissolve the product. The solution was washed 3× with 200 mL of distilled water and 1× with 200 mL of saturated NaCl. The organic layer was dried over anhydrous sodium sulfate and the solvent was removed via rotary evaporation. Residual solvent was removed under vacuum (less than 1 mm Hg) at or slightly above ambient temperature and the structure was confirmed by IR, $^1$HNMR, and $^{13}$CNMR spectroscopy

Example 9

In other experiments, the present inventors have also prepared linear polyester copolymers containing varying amounts of 3-mercaptosuccinic acid and succinic acid with various alkylene diols to afford polyesters with decreased concentration of pendant thiol groups compared to that described in Example 8 above. Crosslinking these polyesters in air on a glass plate for several days at 110° C. afforded polymer films with a wide range of properties. Depending on the ratio of 3-mercaptosuccinic acid to succinic acid, the properties of the polymer films ranged from hard, brittle materials to hard, tough materials to soft, flexible elastomers.

Example 10

In general, crosslinked films swelled in solvents, but were largely insoluble until they underwent hydrolysis, for example, when placed in aqueous acid.

Example 11

In various experiments, crosslinked films degraded upon standing in aqueous acids, such as dilute sulfuric, hydrochloric, and phosphoric acids. The rates of degradation correlated with crosslink density. This property provides materials with controlled rates of degradation for use in a variety of applications.

Example 12

Copolymers containing varying amounts of mercaptosuccinic acid and succinic acid with diols, such as ethylene glycol, 1,2- and 1,3-propanediol, 1,4-butanediol, 1,5-pentanediol, and 1,6-hexanediol, were prepared using the procedures described herein.

The glass transition temperatures of crosslinked films showed decreasing $T_g$ with increasing number of carbons in the diol. As expected, copolymers with a low incorporation of mercaptosuccinic acid tended to give films with low crosslink density. Films, with a low crosslink density, that contained even-numbered diols tended to crystallize readily, while odd-numbered diols crystallized more slowly or not at all. By varying the crosslink density and type of diol used, polymers and copolymers with a wide range of properties have been prepared.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A polymer produced from a monomeric mixture comprising a compound of the formula:

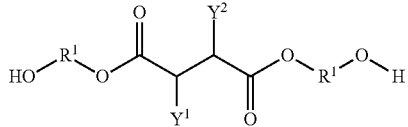

IA wherein
- each of $R^1$ is independently an alkylene, heteroalkylene, arylene, or heteroarylene;
- $Y^a$ is a thiol group; and
- $Y^b$ is a thiol group, and wherein at least some of said thiol groups are cross-linked in said polymer.

2. The polymer of claim 1, wherein each of $R^1$ is independently $C_2$-$C_{20}$ alkylene.

3. The polymer of claim 1, wherein said polymer is a hydrogel.

4. The polymer of claim 1, wherein said polymer is clear colorless or optically translucent.

5. The polymer of claim 1 having a soft and flexible physical characteristic.

6. The polymer of claim 1 having a hard and brittle physical characteristic.

7. The polymer of claim 1, wherein said monomeric mixture further comprises a compound of the formula:

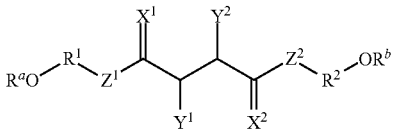

IB wherein
- each of $X^1$, $X^2$, $Z^1$, and $Z^2$ is independently $NR^3$, O, $P(O)_a(OR^z)_b$, Se, or S;
- $Y^1$ is —S(O)—$R^4$;
- $Y^2$ is H, $C_1$-$C_6$ alkyl, or —S(O)—$R^4$;
- a is 0 or 1 such that when a is 0, b is an integer from 1 to 3 and when a is 1, b is 0 or 1;
- n is an integer from 0 to 4;
- each $R^z$ is independently H, or alkyl;
- each of $R^a$ and $R^b$ is independently H, alkyl, aryl, heteroaryl, or a hydroxy protecting group;
- each of $R^{1b}$ and $R^{2b}$ is independently alkylene, heteroalkylene, haloalkylene, cycloalkylene, arylene, or heteroarylene;
- each of $R^3$ is independently H, alkyl, aryl, heteroaryl, or a nitrogen protecting group; and
- each of $R^4$ is independently H, alkyl, aryl, or heteroaryl.

8. The polymer of claim 7, wherein $X^1$ is O.
9. The polymer of claim 7, wherein $X^2$ is O.
10. The polymer of claim 7, wherein $Y^2$ is H or $C_1$-$C_6$ alkyl.
11. The polymer of claim 7, wherein n is 2.
12. The polymer of claim 7, wherein $Z^1$ is O.
13. The polymer of claim 7, wherein $Z^2$ is O.
14. The polymer of claim 7, wherein $R^a$ is H.
15. The polymer of claim 7, wherein $R^b$ is H.
16. The polymer of claim 7, wherein $R^{1b}$ is alkylene.
17. The polymer of claim 7, wherein $R^{2b}$ is alkylene.

* * * * *